(12) United States Patent
Silfverstrand et al.

(10) Patent No.: US 11,850,132 B2
(45) Date of Patent: Dec. 26, 2023

(54) ABSORBENT ARTICLE HAVING AN IMPROVED FASTENING SYSTEM AND A METHOD TO MANUFACTURE SUCH ABSORBENT ARTICLE

(71) Applicant: Essity Hygiene and Health Aktiebolag, Gothenburg (SE)

(72) Inventors: Anders Silfverstrand, Gothenburg (SE); Maria Swedberg, Gothenburg (SE)

(73) Assignee: ESSITY HYGIENE AND HEALTH AKTIEBOLAG, Gothenburg (SE)

(*) Notice: Subject to any disclaimer, the term of this patent is extended or adjusted under 35 U.S.C. 154(b) by 1331 days.

(21) Appl. No.: 16/313,742

(22) PCT Filed: Jul. 5, 2016

(86) PCT No.: PCT/EP2016/065851
§ 371 (c)(1),
(2) Date: Dec. 27, 2018

(87) PCT Pub. No.: WO2018/006946
PCT Pub. Date: Jan. 11, 2018

(65) Prior Publication Data
US 2019/0224054 A1  Jul. 25, 2019

(51) Int. Cl.
*A61F 13/49* (2006.01)
*A61F 13/56* (2006.01)
(Continued)

(52) U.S. Cl.
CPC .. *A61F 13/49058* (2013.01); *A61F 13/15747* (2013.01); *A61F 13/5116* (2013.01);
(Continued)

(58) Field of Classification Search
CPC ............ A61F 13/15747; A61F 13/5116; A61F 13/49058; A61F 13/56; A61F 13/5616;
(Continued)

(56) References Cited

U.S. PATENT DOCUMENTS 4,169,303 A * 10/1979 Lemelson .......... A44B 18/0088
24/446
4,290,174 A *  9/1981 Kalleberg .......... A44B 18/0019
24/444

(Continued)

FOREIGN PATENT DOCUMENTS

| CN | 1296401 A | 5/2001 |
|---|---|---|
| CN | 101346118 A | 1/2009 |

(Continued)

OTHER PUBLICATIONS

International Preliminary Report on Patentability for Application No. PCT/EP2016/065851, dated Jul. 18, 2018—6 pages.

(Continued)

*Primary Examiner* — Michele Kidwell
(74) *Attorney, Agent, or Firm* — BUCHANAN INGERSOLL & ROONEY PC

(57) ABSTRACT

An absorbent article includes a first body portion, a second body portion and a crotch portion located between the first body portion and the second body portion. At least one of the first body portion or the second body portion includes at least one side panel having a multilayered portion. The multilayered portion includes at least a first layer and a second layer. The multilayered portion is obtained by folding the at least one side panel. The first and the second layer of the multilayered portion are connected to each other and the multilayered portion is provided with surface protrusions at one surface of the multilayered portion. The surface protrusions are integrally made of material of the multilay- (Continued)

ered portion. Furthermore, the disclosure relates to manufacturing such an absorbent article.

23 Claims, 7 Drawing Sheets

(51) Int. Cl.
| | |
|---|---|
| *A61F 13/62* | (2006.01) |
| *A61F 13/15* | (2006.01) |
| *A61F 13/58* | (2006.01) |
| *A61F 13/511* | (2006.01) |
| *A61F 13/513* | (2006.01) |
| *B29D 99/00* | (2010.01) |

(52) U.S. Cl.
CPC .. *A61F 13/51104* (2013.01); *A61F 13/51394* (2013.01); *A61F 13/56* (2013.01); *A61F 13/5616* (2013.01); *A61F 13/5622* (2013.01); *A61F 13/62* (2013.01); *B29D 99/0064* (2013.01); *A61F 2013/15715* (2013.01); *A61F 2013/588* (2013.01)

(58) Field of Classification Search
CPC ............ A61F 13/5622; A61F 13/51104; A61F 13/51394; A61F 13/62; A61F 2013/15715; A61F 2013/588; B29D 99/0064
See application file for complete search history.

(56) References Cited

U.S. PATENT DOCUMENTS

| | | | | |
|---|---|---|---|---|
| 4,761,318 | A | * | 8/1988 | Ott .................. B24D 11/02 156/244.11 |
| 5,108,384 | A | * | 4/1992 | Goulait ............... A61F 13/5512 604/389 |
| 5,413,568 | A | | 5/1995 | Roach et al. |
| 5,531,732 | A | | 7/1996 | Wood |
| 5,662,638 | A | * | 9/1997 | Johnson ............... B29C 66/004 604/389 |
| 5,785,699 | A | | 7/1998 | Schmitz |
| 6,007,527 | A | * | 12/1999 | Kawaguchi ......... A61F 13/5512 604/389 |
| 6,036,679 | A | | 3/2000 | Balzar et al. |
| 6,287,665 | B1 | | 9/2001 | Hammer |
| 6,524,294 | B1 | * | 2/2003 | Hilston ................ A61F 13/581 604/389 |
| 6,746,434 | B2 | * | 6/2004 | Johnson ................. A61F 13/82 24/442 |
| 7,018,496 | B1 | | 3/2006 | George et al. |
| 7,744,576 | B2 | | 6/2010 | Busam et al. |
| 7,857,801 | B2 | | 12/2010 | Hamall et al. |
| 8,197,458 | B2 | | 6/2012 | Bäck |
| 8,298,205 | B2 | | 10/2012 | Norrby et al. |
| 8,585,672 | B2 | | 11/2013 | LaVon et al. |
| 8,663,184 | B2 | | 3/2014 | Liu et al. |
| 8,784,722 | B2 | | 7/2014 | Rocha |
| 8,979,815 | B2 | | 3/2015 | Roe et al. |
| 9,216,118 | B2 | | 12/2015 | Roe et al. |
| 9,480,611 | B2 | | 11/2016 | Enz et al. |
| 9,834,355 | B2 | | 12/2017 | Dahlqvist et al. |
| 10,076,162 | B2 | | 9/2018 | Rocha |
| 10,188,588 | B2 | | 1/2019 | Moszner et al. |
| 10,966,878 | B2 | | 4/2021 | Rudén et al. |
| 10,973,711 | B2 | * | 4/2021 | Swedberg ............ B29C 66/1122 |
| 10,993,857 | B2 | * | 5/2021 | Swedberg ............ A61F 13/5512 |
| 11,026,849 | B2 | | 6/2021 | Rudén et al. |
| 2002/0023321 | A1 | | 2/2002 | Clune |
| 2003/0100878 | A1 | * | 5/2003 | Leak .................. A61F 13/622 604/386 |
| 2003/0120253 | A1 | | 6/2003 | Wentzel et al. |
| 2005/0101930 | A1 | * | 5/2005 | Tachauer .............. D04H 13/00 156/182 |
| 2006/0135022 | A1 | * | 6/2006 | Porter ............... B29C 66/72141 442/381 |
| 2008/0038507 | A1 | | 2/2008 | Seth et al. |
| 2008/0289762 | A1 | * | 11/2008 | Blenke ................. C09J 123/12 156/334 |
| 2010/0108251 | A1 | | 5/2010 | Malowaniec |
| 2010/0180407 | A1 | * | 7/2010 | Rocha .................. B29C 59/04 264/444 |
| 2010/0262111 | A1 | | 10/2010 | Lindstrom |
| 2013/0090618 | A1 | | 4/2013 | Alshammari |
| 2016/0082688 | A1 | * | 3/2016 | Nakai ................... B32B 27/16 264/293 |
| 2017/0087034 | A1 | | 3/2017 | Bosser |
| 2018/0104037 | A1 | | 4/2018 | Johnson |
| 2019/0016058 | A1 | | 1/2019 | Tuma |
| 2019/0254890 | A1 | | 8/2019 | Yonaha |
| 2020/0214907 | A1 | | 7/2020 | Bremer et al. |

FOREIGN PATENT DOCUMENTS

| | | |
|---|---|---|
| CN | 101500521 A | 8/2009 |
| CN | 101534778 A | 9/2009 |
| CN | 101641066 A | 2/2010 |
| CN | 101848691 A | 9/2010 |
| CN | 102341228 A | 2/2012 |
| CN | 102939062 A | 2/2013 |
| CN | 105517515 A | 4/2016 |
| CN | 106170276 A | 11/2016 |
| DE | 10102501 A1 | 8/2002 |
| DE | 10-2016-000756 A1 | 7/2017 |
| EP | 1529506 A1 | 5/2005 |
| EP | 2926787 A1 | 10/2015 |
| EP | 3047826 A1 | 7/2016 |
| EP | 3047827 A1 | 7/2016 |
| JP | H10511868 A | 11/1998 |
| JP | 2000-000269 A | 1/2000 |
| JP | 2003-535649 A | 12/2003 |
| JP | 2014104147 A | 6/2014 |
| JP | 2015-058326 A | 3/2015 |
| RU | 2395265 C1 | 7/2010 |
| RU | 2396932 C1 | 8/2010 |
| RU | 2400199 C2 | 9/2010 |
| RU | 2404057 C2 | 11/2010 |
| RU | 2 518 212 C2 | 6/2014 |
| TW | 201545729 A | 12/2015 |
| WO | 8804546 A1 | 6/1988 |
| WO | 95/30397 A1 | 11/1995 |
| WO | 96/20675 A1 | 7/1996 |
| WO | 99/53881 A1 | 10/1999 |
| WO | 00/27236 A1 | 5/2000 |
| WO | 0197738 A2 | 12/2001 |
| WO | 0226182 A2 | 4/2002 |
| WO | 2008060204 A1 | 5/2008 |
| WO | 2009061241 A1 | 5/2009 |
| WO | 2009/136826 A1 | 11/2009 |
| WO | 2010071517 A1 | 6/2010 |
| WO | 2010/085492 A1 | 7/2010 |
| WO | 2011037502 A1 | 3/2011 |
| WO | 2011162657 A1 | 12/2011 |
| WO | 2011162658 A1 | 12/2011 |
| WO | 2012100823 A1 | 8/2012 |
| WO | 2013/162430 A1 | 10/2013 |
| WO | 2015/190964 A1 | 12/2015 |
| WO | 2015190966 A1 | 12/2015 |
| WO | 2016/081438 A1 | 5/2016 |
| WO | 2016/149243 A1 | 9/2016 |
| WO | 2018228682 A1 | 12/2018 |
| WO | 2018228710 A1 | 12/2018 |
| WO | 2019120574 A1 | 6/2019 |

OTHER PUBLICATIONS

International Search Report and Written Opinion for Application No. PCT/EP2016/065851, dated Feb. 15, 2017—8 pages.

Non-Final Office Action issued by the U.S. Patent and Trademark Office in U.S. Appl. No. 16/314,234 dated Oct. 8, 2020, U.S. Patent and Trademark Office, Alexandria, VA. (10 pages).

(56) References Cited

OTHER PUBLICATIONS

Notice of Allowance dated Dec. 21, 2020, by the U.S. Patent and Trademark Office in U.S. Appl. No. 16/956,238. (10 pages).
Notification of the First Office Action dated Dec. 16, 2020, by the National Intellectual Property Administration (CNIPA) of the People's Republic of China in Chinese Patent Application No. 201780097814.3 and an English translation of the Office Action. (23 pages).
Brazil Office Action for Brazil Application No. BR112018076381-0, dated May 18, 2020, 4 pages.
Decision to Grant dated Oct. 26, 2020, by the Federal Service for Intellectual Property in Russian Patent Application No. 2020124162 and an English translation of the Decision. (21 pages).
Office Action dated Nov. 30, 2020, by the U.S. Patent and Trademark Office in U.S. Appl. No. 16/955,895. (14 pages).
Office Action (Notification of the First Office Action) dated Dec. 4, 2020 by the China National Intellectual Property Administration (CNIPA) of the Peoples Republic of China in corresponding Chinese Patent Application No. 201780097815.8, and an English Translation of the Office Action. (23 pp.).
Chinese Office Action for Chinese Application No. 201680087419.2, dated Jun. 28, 2019, with translation, 16 pages.
Russian Decision to Grant a Patent for Russian Application No. 2019101795, dated May 24, 2019, with translation, 13 pages.
Notice of Reasons for Rejection for Japanese Application No. 2019-500234, dated Dec. 16, 2019, with translation, 5 pages.
International Search Report (PCT/ISA/210) and Written Opinion (PCT/ISA/237) dated Aug. 16, 2019, by the European Patent Office as the International Searching Authority for International Application No. PCT/EP2018/084729.
International Preliminary Report on Patentability (PCT/IPEA/409) dated Mar. 10, 2021, by the European Patent Office as the International Searching Authority for International Application No. PCT/EP2018/084729.
Written Opinion of the International Preliminary Examining Authority (PCT/IPEA/408) dated Nov. 4, 2020, by the European Patent Office as the International Searching Authority for International Application No. PCT/EP2018/084729.
Office Action (Decision to Grant a Patent) dated Jul. 22, 2020, by the Japanese Patent Office in corresponding Japanese Patent Application No. 2019-500234, and an English Translation of the Office Action. (5 pages).
Chinese Office Action for Chinese Application No. 201680087410.1, dated Jan. 19, 2020, with translation, 17 pages.
Chinese Office Action for Chinese Application No. 201680087410.1, dated Jul. 15, 2019, with translation, 22 pages.
International Search Report (PCT/ISA/210) dated Feb. 21, 2018, by the European Patent Office as the International Searching Authority for International Application No. PCT/EP2017/084476, 2 pages.
International Search Report and Written Opinion for Application No. PCT/EP2016/065862, dated Feb. 16, 2017, 10 pages.
Written Opinion (PCT/ISA/237) dated Feb. 21, 2018, by the European Patent Office as the International Searching Authority for International Application No. PCT/EP2017/084476, 6 pages.
International Preliminary Report on Patentability (PCT/IPEA/409) dated Mar. 30, 2020, by the European Patent Office as the International Preliminary Examining Authority for International Application No. PCT/EP2017/084479, 13 pages.
International Preliminary Report on Patentability (PCT/IPEA/409) dated Feb. 27, 2020, by the European Patent Office as the International Preliminary Examining Authority for International Application No. PCT/EP2017/084476, 7 pages.
Written Opinion (PCT/IPEA/408) dated Nov. 15, 2019, by the European Patent Office as the International Preliminary Examining Authority for International Application No. PCT/EP2017/084479, 8 pages.
International Search Report (PCT/ISA/210) and Written Opinion (PCT/ISA/237) dated Jun. 27, 2018, by the European Patent Office as the International Searching Authority for International Application No. PCT/EP2017/084479, 9 pages.
Chinese Office Action for Chinese Application No. 201680087410.1, dated May 15, 2020, with translation, 26 pages.
European Office Action for European Application No. 16734682.4, dated Jun. 19, 2019, 3 pages.
International Preliminary Report on Patentability for Application No. PCT/EP2016/065862, dated Jul. 11, 2018, 6 pages.
Office Action dated Aug. 11, 2022, by the Brazilian Patent Office in corresponding Brazilian Patent Application No. BR112018076381-0, and an English Translation of the Office Action. (6 pages).
Decision to Grant a Patent for Invention dated Nov. 24, 2020, by the Federal Service for Intellectual Property (ROSPATENT) in corresponding Russian Patent Application No. 2020124121 and an English translation of the Decision. (21 pages).

\* cited by examiner

ABSORBENT ARTICLE HAVING AN IMPROVED FASTENING SYSTEM AND A METHOD TO MANUFACTURE SUCH ABSORBENT ARTICLE

CROSS REFERENCE TO RELATED APPLICATIONS

This is a U.S. National Phase application of PCT/EP2016/065851, filed Jul. 5, 2016, the disclosure of which is incorporated herein by reference in its entirety for all purposes.

TECHNICAL FIELD

The invention relates to an absorbent article having an improved fastening system. The invention also relates to a method to manufacture such absorbent article.

BACKGROUND

Various types of fastening systems for connecting or holding together portions of absorbent articles and/or for securing an absorbent article upon a wearer of an absorbent article are known in the art. Easy removal of an absorbent article and/or easy adjustment of an absorbent article during use are high desired.

Examples of refastening systems comprise adhesive tapes and hook-and-loop fastening systems. Hook-and-loop fastening systems are for example sold under the trademark Velcro®. Hook-and-loop fasteners generally comprise two strips which are attached (sewn, glued, heat sealed, . . . ) to the opposing surfaces to be fastened. The first strip comprises hook, the second strip comprises loops. When the two strips are pressed together, the hooks catch in the loops and the two strips fasten.

The two strips are manufactured in a separate process by extrusion or injection of a thermoplastic melt. Such manufacturing process of the strips is expensive for example because the process requires an expensive equipment and high energy consumption. Such hook-and-loop systems have further drawbacks as they do not provide enough flexibility and softness and may cause discomfort to the wearer. Furthermore the edges or corners of such hook-and-loop systems may inadvertently rub against the wearer during use also causing discomfort.

Therefore, prior to the present invention, there was a need for an improved fastening system for absorbent articles.

SUMMARY

It is an object of the present disclosure to provide an absorbent article having an improved fastening system.

It is another object of the present disclosure to provide an absorbent article which is economical to manufacture.

It is a further object of the present disclosure to provide an absorbent article capable of being loosened or tightened when desired during wear.

It is still a further object of the present disclosure to provide an absorbent article which does not cause undue discomfort to the wearer of the absorbent article.

Furthermore it is an object of the present disclosure to provide a method of manufacturing such an absorbent article.

According to a first aspect of the present disclosure an absorbent article having an improved fastening system is provided. The absorbent articles has a longitudinal direction, a longitudinal center line extending along the longitudinal direction and a lateral direction and comprises a first body portion, a second body portion and a crotch portion located between said first body portion and the second body portion. The first body portion comprises, for example, the front portion whereas the second body portion comprises the rear portion, or vice versa. Preferably, the first body portion and/or the second body portion comprises a waist portion. At least one of the first body portion or the second body portion comprises at least one side panel or is adapted to be provided with at least one side panel. The at least one side panel comprises a lateral side edge and comprises at least one multilayered portion. The at least one multilayered portion comprises at least a first layer and a second layer and comprises a first surface and a second surface. The at least one multilayered portion is preferably obtained by folding the side panel or part of the side panel. Preferably, the different layers of the at least one multilayered portion are connected to each other. At least part of the first surface of the at least one multilayered portion is provided with surface protrusions. The surface protrusions are integrally made of material of the multilayered portion, i.e. of material of the first and the second layer of the multilayered portion. Possibly also the second surface of the at least one multilayered portion is provided with surface protrusions.

Preferably, the different layers of the at least one multilayered portion are connected to each other and the surface protrusions on at least part of the first surface of the at least one multilayered portion is obtained by a softening and forming operation. Preferably, the at least one multilayered portion is subjected to a softening and forming operation to simultaneously connect the layers of the multilayered portion and to provide at least part of the first surface of the at least one multilayered portion with surface protrusions.

"Absorbent articles" refer to consumer products which absorb and contain body exudates, and more specifically, refers to products which are placed against or in proximity to the body of the wearer to absorb and contain the various exudates discharged from the body. Absorbent articles, comprise, for example, diapers and incontinence devices. Diapers comprise for example all-in-one diapers, pant diapers and belt diapers. The diapers can be diapers for babies, young children or adults.

So-called all-in-one diapers are characterized in that they include fastening tabs with which the front and rear portion of the diaper are joined when the diaper is applied around the waist of a user.

So-called pant diapers are characterized in that the front and rear portion of the diaper are joined at the waist. This type of diaper is intended to be put on a user precisely like a pair of underpants, i.e. drawn over the user's legs. The joining at the waist part of the pant diapers can usually be broken open to remove the pant diapers from the user so that is not required to pull the pants down over the user's legs and feet to remove the pant diaper. Pant diapers normally comprise both elastic areas in the waist section and around the leg openings. Pant diapers that can be opened and reclosed by means of refastening means also exist. Such pant diapers can be opened for example to check the contents of the article or to adjust the width of the article and then reclosed afterwards.

So-called belt diapers are characterized in that they comprise a belt that is transverse oriented in relation to the absorbent part of the diaper and which is attached integrally with the chassis or the absorbent part. The belt may have two belt portions extending on either side of the rear end or the front end of the chassis or the absorbent part. When putting on a belt diaper, the two belt portions are intended to be fastened around the waist of the wearer in a first stage. The front end or the rear end of the absorbent part of the belt diaper is hanging loose from the belt between the legs of the wearer. Once the belt portions have been joined together, the absorbent part is led between the user's legs and fastened to the belt, wherein the belt comprises fixing surfaces intended to stick to a fixing element arranged on the absorbent part of the diaper by its free transverse edge. This type of article is particularly useful for caregivers who care for patients that may have dementia or the like. Another type of belt diaper is in two pieces and comprises a separate belt and a separate absorbent structure. When in use the belt is fastened around the user's waist, following which the absorbent structure is joined to the outside of the belt by means of hook and loop elements or tape elements in the corners of the absorption structure.

The absorbent article according to the present disclosure can be a disposable article or a non-disposable article. The term "disposable" is used to describe absorbent articles which generally are not intended to be laundered or otherwise restored, or reused as an absorbent article, e.g., they are intended, to be discarded after a single use and may also be configured to be recycled, composted or otherwise disposed of in an environmentally compatible manner.

The term "longitudinal" or "longitudinally" relates to the length or the lengthwise direction, and in particular the direction running between the first body part and the second body part of the article or between the front and the back of the user.

The term "lateral" or "laterally" relates to the width or widthwise direction, and corresponds with the direction perpendicular to the longitudinal direction. The lateral direction is running from side to side, and in particular from the left to the right of the user, and vice versa.

As described above at least one side panel of the absorbent article according to an aspect of the present invention is provided with at least one multilayered portion. A side panel can be part of the first of the second body portion or can be a laterally extension of the first or the second body portion, for example a fastening tab or a belt portion. The side panel can for example be glued or welded to the first or the second body portion.

The at least one multilayered portion comprises at least two layers, i.e. at least a first layer and a second. In particular embodiments the multilayered lateral side portion comprises three, four, five or even more layers.

Possibly a side panel is provided with more than one multilayered portion, for example with two, three, four, five or even more multilayered portions.

A multilayered portion can be obtained by folding the side panel or by folding part of the side panel. Any type of folding of the side panel can be considered. Examples comprise single folding, double folding and accordion folding such as Z folding. By single folding a multilayered portion comprising two layers is obtained, by double folding a multilayered portion comprising four layers is obtained, by accordion folding a multilayered portion comprising four or more layers is obtained, by Z-folding a multilayered portion comprising three layers is obtained.

It is possible to provide a side panel with at least one multilayered portion before attaching the side panel to the first body portion or to the second body portion. Alternatively, it is possible to provide a side panel with at least one multilayered portion in line in the manufacturing process of the absorbent article.

In a particular embodiment, the multilayered portion is obtained by folding at least a portion of the side panel (for example the lateral side portion of the side panel) towards the longitudinal center line, i.e. inwards towards the longitudinal center line. In such embodiment, the multilayered portion comprises a multilayered lateral side portion. It can be preferred that the multilayered lateral side portion is obtained by folding a portion of the side panel, for example the lateral side portion of the side panel towards the longitudinal center line along a line parallel or substantially parallel with the longitudinal center line. In case the multilayered lateral side portion comprises more than two layers, the multilayered lateral side portion is preferably obtained by double or triple folding the side panel or a part of the side panel.

In another embodiment the multilayered portion is obtained by accordion folding, for example Z-folding, part of the side panel, either a part situated at the lateral side of the side panel or a central part of the side panel.

It is clear that a side panel may comprise more than one accordion folded portion, for example Z-folded multilayered portions.

By providing the side panel with at least one multilayered portion, the material present of the side panel is locally increased so that more material is present to provide the side panel with surface protrusions. By providing the side panel with at least one multilayered portion, a side panel (for example a belt) having less basis weight material can be used.

Furthermore, the at least one multilayered portion may function as a finger lift portion helping the care giver to find the opening of the absorbent product and to fasten the surface protrusions to a landing zone or to remove them from a landing zone. The surface protrusions are adapted to be fastened to a zone of the absorbent article referred to as the landing zone. A multilayered portion is in particular suitable as finger lift portion if it the surface protrusions are arranged at a small distance from the edge, for example at a small distance from the lateral side edge of a side panel. By arranging the surface protrusions at a distance from the lateral side edge of a side panel a part of the multilayered portion will not connect to the landing zone. A user is allowed to grasp the finger lift portion with his/her fingers.

As mentioned, the at least one multilayered portion is subjected to a softening and forming operation to simultaneously connect the different layers of the at least one multilayered portion and to provide at least part of the first surface of the at least one multilayered portion with surface protrusions. Possibly, also the second surface of the at least one multilayered portion is provided with surface protrusions. The surface protrusions are integrally made of material of the layers of the multilayered portion. As the surface protrusions are integrally made of the material of the multilayered portion, there is no risk that surface protrusions such as hooks come loose during use of the absorbent article. This is an important advantage compared to absorbent articles provided with hooks known in the prior art.

The surface protrusions are adapted to be fastened to a zone of the absorbent article, referred to as the landing zone. For the landing zone, any type of zone that is able to engage and preferably able to releasably engage with the surface protrusions can be considered. A landing zone can be a zone attached to the absorbent article for example to one or more side panels of the absorbent article. Examples comprise a loop patch or a non-woven, woven or knitted patch attached to the absorbent article for example by gluing, melting or stitching. Alternatively, the material of the absorbent article, or the material of part of the absorbent article, for example, the material of one or more side panels, can act as landing zone, for example, if the absorbent article or part of the absorbent article, for example, one or more side panels, comprises a non-woven.

The surface protrusions can have any shape. Preferred examples of surface protrusions comprise pins, for example straight pins, angled pins, curved pins, tapered pins, limbed or multi-limbed pins, hooks, limbed or multi-limbed hooks, mushroom shaped protrusions, palm tree shaped protrusions. The surface protrusions may have any type of cross-section such as round, oval, square, rectangular, polygonal. The surface projections preferably have a solid core.

Within one multilayered portion all surface protrusions may have the same shape. Alternatively, one multilayered portion may comprise several different shapes of surface protrusions.

When a side panel of an absorbent article has several multilayered portions provided with surface protrusions, the different multilayered portions can have the same shapes of surface protrusions or the different multilayered portions can have different shapes of surface protrusions.

The number of surface protrusions ranges preferably between 100 and 500 surface protrusions per $cm^2$, and more preferably between 166 and 408 surface protrusions per $cm^2$.

Within one multilayered portion the number of surface protrusions per $cm^2$ can be constant or the number of surface protrusions can vary over the multilayered portion.

When a side panel of an absorbent article has several multilayered portions provided with surface protrusions, the different multilayered portions can have the same number of surface protrusions per $cm^2$, or the different multilayered portions can have a different number of surface protrusions per $cm^2$.

In preferred embodiments, the second surface of the at least one multilayered portion is provided with at least one visual indication. The at least one visual indication is preferably obtained by the softening and forming operation to connect the different layers of the multilayered portion to each other and to provide the multilayered portion with surface protrusions. This means that one operation allows to connect the different layers of the multilayered portion, to provide the multilayered portion with surface protrusions at its first surface and to provide the multilayered portion with at least one visual indication at the second surface.

By arranging the surface protrusions on the first surface of a multilayered portion in a certain pattern, for example in the pattern of an arrow, a visual indication can be obtained on the second surface of the multilayered portion, this since the material on the second surface changes because the material in the multilayered portion melts in the area of the surface protrusions during the softening and forming operation. Such visual indication can, for example, give instructions to the care giver how to open the side panel of the absorbent article.

The side panel of the article preferably comprises, for example, a polymer film or foil, a coated film or foil, for example a polymer coated film or foil, a textile substrate such as a woven structure or a non-woven substrate or a coated textile substrate, for example a polymer coated textile structure. The side panel preferably comprises a thermoplastic material. Examples of thermoplastic materials comprise polyamide, polyolefin such as polypropylene and polyethylene, polystyrene such as styrene-isoprene-styrene (SIS), styrene-butadiene-styrene (SBS), styrene-ethylene-styrene (SBS), acrylonitrile-butadiene-styrene (ABS), polyester, polycarbonate, polyvinyl chloride (PVC), polyetherester, polyetheramine and blends thereof.

The thermoplastic material may be modified or reinforced for example with fillers, fibers, flame retardants, colorants, etc.

It is clear for a person skilled in the art that the side panel may comprise multiple layers for example a laminate comprising two or three layers.

Compared to absorbent articles known in the art, an absorbent article provided with a fastening system according to an aspect of the present invention has the advantage not requiring the use of adhesive, for fastening for example a hook and loop system to the absorbent article, resulting in a lower foot print.

An important advantage of absorbent articles according to an aspect of the present invention is the fact that the absorbent article will be more intuitive to handle for the consumer or the care giver due to the fact that it is possible to have a visual indication and/or an integrated finger lift portion. Even if the surface protrusions are not in a specific pattern, the material on the opposite side of the surface protrusions will change due to the softening and forming operation which helps the user, the care taker or the care giver to easily find the multilayered portions. The material in the area which is exposed to the softening and forming operation will melt and the structure and/or color may change compared to the material of the multilayered portion.

As the side panel or side panels is/are provided with a multilayered portion, it is not required to provide the absorbent article with thicker side panels.

A further advantage of absorbent articles according to an aspect of the present invention compared to absorbent articles known in the art provided with hook-and-loop fastening means is that there is no risk that the fastening means or the hooks of the fastening means come loose for example because of bad adhesion. The risk that the child or incontinent adult is getting the loose parts in his mouth is hereby considerably reduced.

Furthermore the comfort of the user is increased as the flexibility and softness of the fastening system of an absorbent article according to an aspect of the present invention is increased compared to absorbent articles known in the art provided with hook-and-loop fastening means.

Additionally, the side panels can be provided with visual indications for example indications giving instructions to the user how to open and reclose the side panels, for example the fastening tabs of the belt portions of an absorbent article. As the visual indications are obtained by the operation step to provide the side panels with the surface protrusions the application of the visual indication do not increase the manufacturing costs.

The visual indications are of particular importance for belt diapers. For the belt diapers known in the art it is hard for the care giver to find the opening of the belt portions and it is hard to understand how to use the belt diaper, more particularly the belt portions of the belt diaper. The visual indication or visual indications of a multilayered portion according to an aspect of the present invention may help to find the opening of the belt portions and may give instructions to the care giver how to use the belt diaper and in particular the belt portions of the belt diaper without increasing the material costs or the costs for manufacturing.

According to a second aspect of the invention a method to provide an absorbent article with an improved fastening system is provided. The method comprises the steps of
providing an absorbent article, the absorbent article having a longitudinal direction, a longitudinal center line extending along the longitudinal direction and a lateral direction, the absorbent article comprising a first body portion, a second body portion and a crotch portion located between the first body portion and the second body portion, at least one of the first body portion or the second body portion comprising at least one side panel or at least one of the first body portion or the second body portion being adapted to be provided with at least one side panel, the at least one side panel having a lateral side edge;

providing the at least one side panel with at least one multilayered portion by folding the at least one side panel or part of the at least one side panel, said at least one multilayered portion comprising at least a first layer and a second layer and comprising a first surface and a second surface;

providing a forming die having a surface provided with a plurality of cavities, at least some of the cavities having a shape to produce protrusions, bringing the first surface of the at least one multilayered portion of the at least one side panel in contact with the surface of the forming die provided with a plurality of cavities;

applying energy to the at least one multilayered portion to soften and form at least part of the at least one multilayered portion in such a way that the first layer and the second layer of the at least one multilayered portion connect and that material of the at least one multilayered portion is forced into the cavities of the forming die to provide the first surface of the at least one multilayered portion with surface protrusions. The connection of the first layer and of the second layer and the formation of the surface protrusion are preferably obtained in one process step.

Possibly, also the second surface of the at least one multilayered portion is provided with surface protrusions.

The energy is for example applied by means of a source selected of a group consisting of induction heating, ultrasonic vibrations, micro waves and infrared waves. Preferably, the energy is applied by means of ultrasonic vibrations.

The surface protrusions are for example obtained by using a method as described in DE10102501 or as described in U.S. Pat. No. 8,784,722.

It can be preferred to apply a mask between the at least one multilayered portion and the forming die to provide the at least one multilayered portion with surface protrusions in a pattern.

The multilayered portion can be obtained by any type of folding known in the art, for example by single folding, double folding, accordion folding such as Z-folding.

The multilayered portion can be a multilayered lateral side portion located at the lateral side edge of a side panel or can be a multilayered portion that is located anywhere between the lateral side edge and the other end of a side panel, for example at the center of a side panel.

It is clear that a side panel may comprise more than one multilayered portions, for example two, three, four or five accordion folded, for example Z-folded multilayered portions.

BRIEF DESCRIPTION OF THE DRAWINGS

Embodiments of the invention will now be described into more detail with reference to the accompanying drawings of which

DETAILED DESCRIPTION OF PARTICULAR EMBODIMENTS

Figure 1:
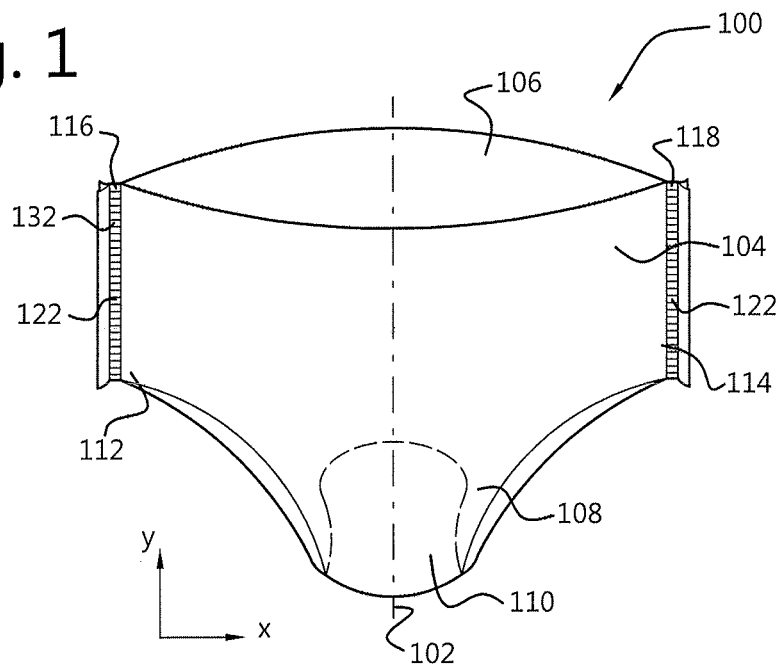
FIG. 1 shows a pant diaper according to an embodiment of the present invention.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn to scale for illustrative purposes. The dimensions and the relative dimensions do not correspond to actual reductions to practice of the invention.

FIG. 1 shows a first embodiment of an absorbent article according to the present invention in the form of a pant diaper 100 for children or incontinent adults. The pant diaper 100 comprises a first body portion 104, a second body portion 106, and a crotch portion 108 between the first body portion 104 and the second body portion 106. In use, the first body portion 104 (also referred to as the front portion) is located on the user's abdomen, whereas the second body portion 106 (also referred to as the rear portion) is located on the user's back.

The pant diaper 100 has a longitudinal direction, marked in FIG. 1 with Y, and a lateral direction, marked in FIG. 1 with X. The pant diaper 100 has a longitudinal center line 102 extending along the longitudinal direction Y.

Preferably, an absorbent core 110 is disposed in the crotch portion 108. The absorbent core 110 is possibly extending in the first body portion 104 and in the second body portion 106.

The first body portion 104 comprises two laterally extending side panels 112, 114. The second body portion 106 comprises two laterally extending side panels 116, 118. The side panels 112, 114 of the first body portion 104 are releasably connected to the side panels 116, 118 of the second body portion 106. At least the side panels 112, 114 of the first body portion 104 comprise a multilayered portion 122, for example a multilayered lateral side portion 122. The multilayered portion 122 of the side panels 112, 114 is for example obtained by folding the side panel 112 as for example shown in FIGS. 4A, 4B and 4C. Alternatively, the multilayered portion 122 can be obtained by folding a side panel 112, 114 as, for example, shown in FIGS. 6A, 6C and 6E. The multilayered lateral side portion 122 of the side panels 112, 114 is provided with surface protrusions 132 which are adapted to releasably engage with a landing zone. The side panels 116, 118 corresponding with the side panels 112, 114 are provided with such a landing zone. In case the side panels 116, 118 comprise a woven material, the woven material of the side panels 116, 118 can as such act as landing zone.

By providing the side panels 112, 114 of the first body portion 104 of a pant diaper 100 with a multilayered portion 122 provided with surface protrusions 132 and by providing the side panels of the zone 116, 118 with at least one landing zone (not shown), the pant diaper 100 can be opened for example to check the contents or to adjust the width of the pant diaper 100 and can be reclosed thereafter.

Figure 2:
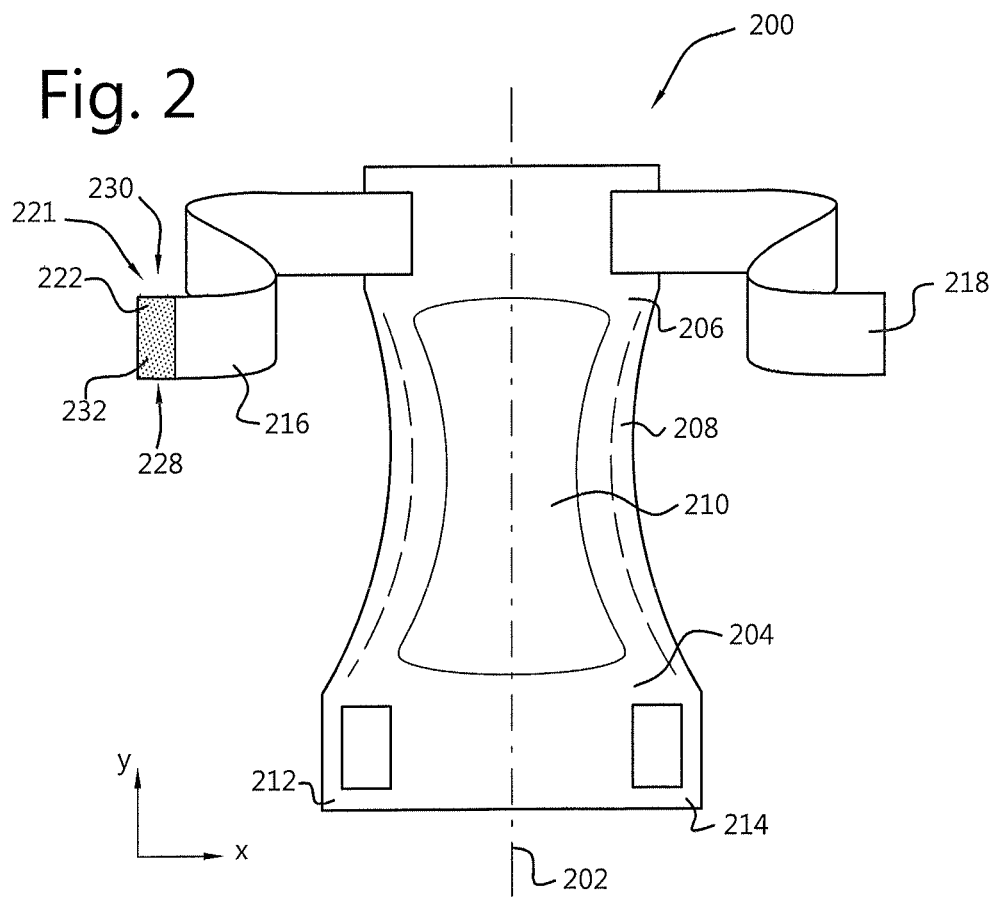
FIG. 2 shows a belt diaper according to an embodiment of the present invention.

FIG. 2 shows a second embodiment of an absorbent article according to the present invention in the form of a belt diaper 200. The belt diaper 200 comprises a first body portion 204, a second body portion 206 and a crotch portion 208 between the first body portion 204 and the second body portion 206. In use, the first body portion 204 (also referred to as the front portion) is located on the user's abdomen, whereas the second body portion 206 (also referred to as the rear portion) is located at the user's back.

The belt diaper 200 has a longitudinal direction, marked in FIG. 2 with Y, and a lateral direction, marked in FIG. 2 with X. The belt diaper 200 has a longitudinal center line 202 extending along the longitudinal direction Y.

Preferably, an absorbent core 210 is disposed in the crotch portion 208. The absorbent core 210 is possibly extending in the first body portion 204 and in the second body portion 206.

The first body portion 204 comprises two side panels 212, 214. Preferably the two side panels 212, 214 consist of the same material as the first body portion 204. The second body portion 206 comprises two side panels 216, 218, exemplified as two laterally extending belt portions 216, 218. The laterally extending belt portions 216, 218 of the second body portion 208 are for example attached to the waist portion of the second body portion 208 by welding or gluing. Alternatively the laterally extending belt portions 216, 218 can consist of the same material as the second body portion 206. The laterally extending belt portions 216, 218 are intended to be wrapped around the waist of the user of the belt article 200, and are fastened together by means of a fastening means 221. At least one of the laterally extending belt portions 216, 218 of the second body portion 206 comprises fastening means 221. In the embodiment shown in FIG. 2, belt portion 216 is provided with fastening means 221.

Figure 4A:
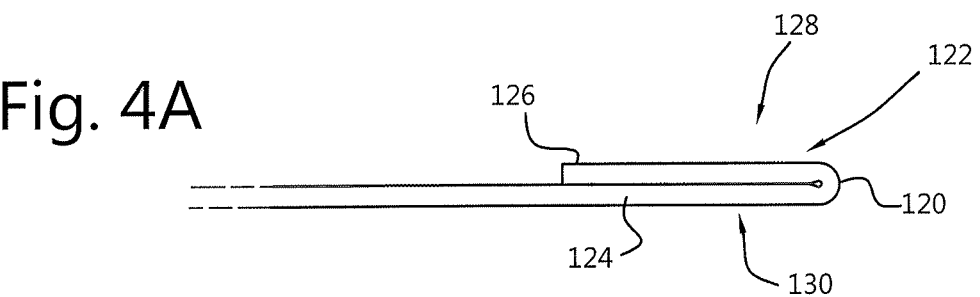
FIGS. 4A, 4C and 4E show three different embodiments of folding a side panel to obtain a multilayered lateral side portion.
Figure 4B:
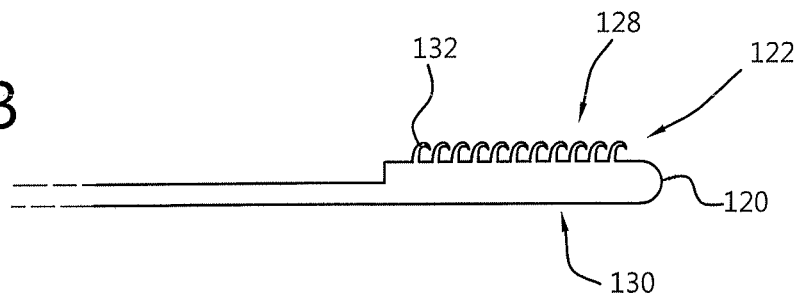
FIGS. 4B, 4D and 4F show the multilayered portions of FIGS. 4A, 4C and 4F subjected to a softening and forming operation.
Figure 4C:
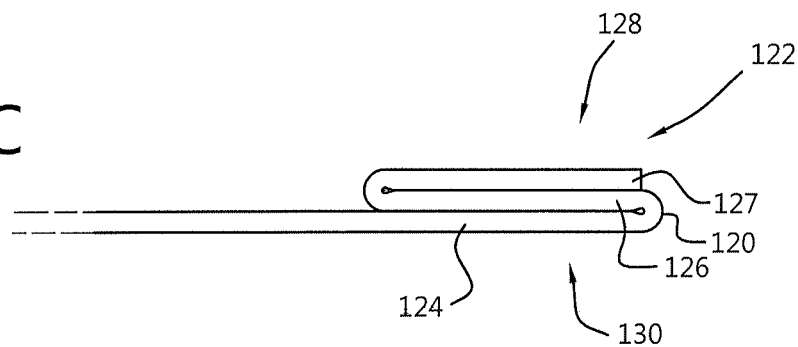
Figure 6A:
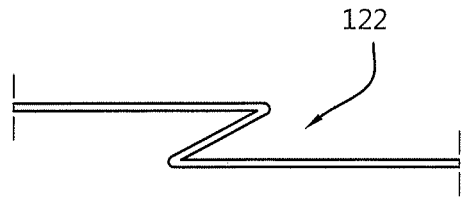
FIGS. 6A, 6C and 6E show three different embodiments of Z-folding to obtain a multilayered portion.
Figure 6B:
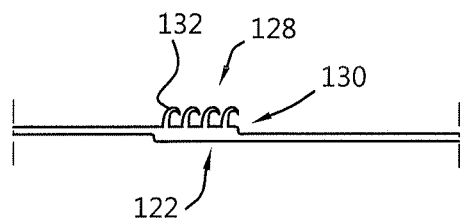
FIGS. 6B, 6D and 6F show the multilayered portions of FIGS. 6A, 6C and 6E subjected to a softening and forming operation.
Figure 6C:
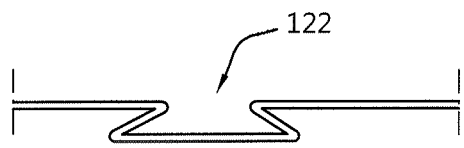
Figure 6D:
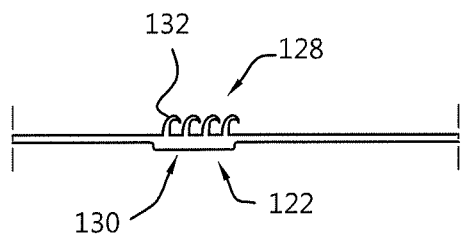
Figure 6E:

The fastening means 221 comprises a multilayered portion 222, for example a multilayered portion 222 as shown in FIG. 4A, 4B, or 4C, or a multilayered portion 222, as shown in FIG. 6A, 6C or 6E. The multilayered portion 222 comprises a first surface 228 and a second surface 230. The first surface 228 of the multilayered portion 222 is provided with surface protrusions 232 integrally formed from the material of the multilayered portion 222.

It is possible to provide at least one of the belt portions 216, 218 with a multilayered portion 222 before attaching the at least one belt portion 216, 218 to the second body portion 206. Alternatively, it is possible to provide at least one of the belt portions 216, 218 with a multilayered portion 222 in-line during the manufacturing process of the belt diaper 200.

To fasten the laterally extending belt portions 216, 218, the laterally extending belt portions 216, 218 are wrapped around the waist of the user of the belt article 200 and the surface protrusions 232 of the multilayered portion 222 of belt portion 216 are releasably engaged with a landing zone of the belt portion 218. In case the belt portion 218 comprises a woven material, the woven material can as such act as landing zone.

Figure 3:
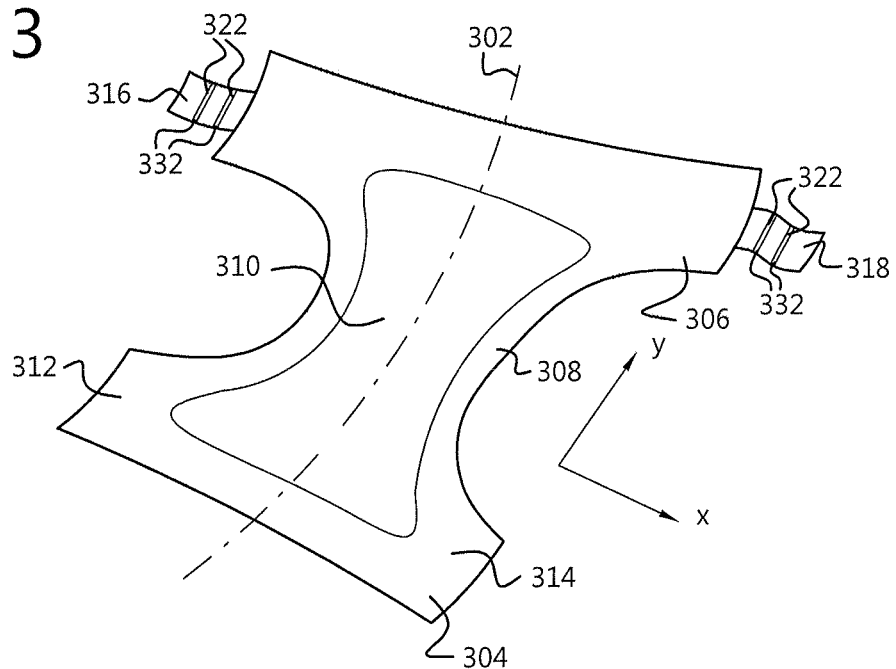
FIG. 3 shows an all-in-one diaper according to an embodiment of the present invention.

FIG. 3 shows a third embodiment of an absorbent article according to the present invention in the form of an all-in-one diaper 300. The all in-in-one diaper 300 comprises a first body portion 304, a second body portion 306 and a crotch portion 308 between the first body portion 304 and the second body portion 306. In use, the first body portion 304 (also referred to as the front portion) is located on the user's abdomen, whereas the second body portion 306 (also referred to as the rear portion) is located at the user's back.

The all-in-one diaper 300 has a longitudinal direction, marked in FIG. 3 with Y, and a lateral direction, marked in FIG. 3 with X. The all-in-one diaper 300 has a longitudinal center line 302 extending along the longitudinal direction Y.

Preferably, an absorbent core 310 is disposed in the crotch portion 308. The absorbent core 310 is possibly extending in the first body portion 304 and in the second body portion 306.

Figure 6F:
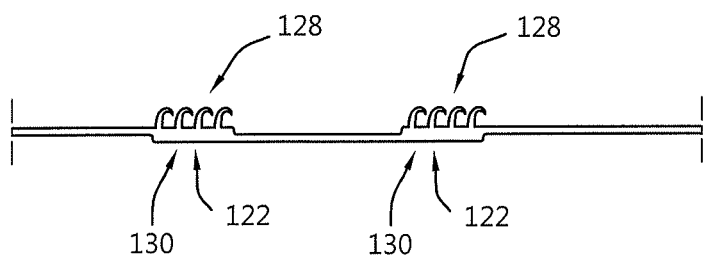

The first body portion 304 comprises two side panels 312, 314. Preferably the two side panels 312, 314 consist of the same material as the first body portion 304. The second body portion 306 comprises two side panels 316, 318, more particularly, two laterally extending fastening tabs 316, 318. The laterally extending fastening tabs 316, 318 of the second body portion 308 are, for example, attached to the waist portion of the second body portion 308 by welding or gluing. The laterally extending fastening tabs 316, 318 are intended to fasten the second body portion 306 to the first body portion 304. The laterally extending fastening tabs 316, 318 comprise one or more multilayered portions 322 provided with surface protrusions 332. The multilayered portion(s) 322 may comprise a multilayered portion as shown in FIG. 4A, 4B or 4C, or may alternatively comprise one or more multilayered portions as shown in FIGS. 6B, 6D and 6F.

It is possible to provide the laterally extending tabs 316, 318 with one or more multilayered portions 322 before attaching the laterally extending tables 316, 318 to the second body portion 306. Alternatively, it is possible to provide laterally extending tables 316, 318 with one or more multilayered portions 322 in-line during the manufacturing process of the all-in-one diaper 300.

The first body portion 304 is provided with at least one landing zone (not shown) on the outer cover of the all-in-one diaper 300 allowing the engagement, preferably releasably engagement, of the surface protrusions 332 of the multilayered portion 322 of the fastening tabs 316, 318 of the second body portion 306. In case the first body portion 304 comprises a non-woven material, the non-woven material of the first body portion 304 can act as landing zone.

Figure 4D:
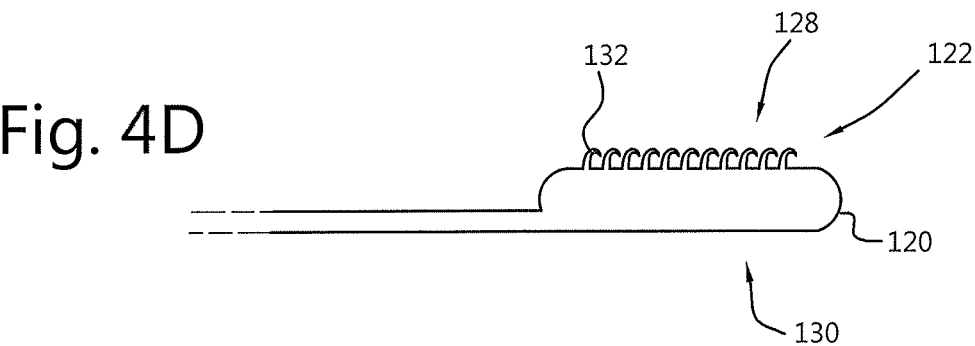
Figure 4E:
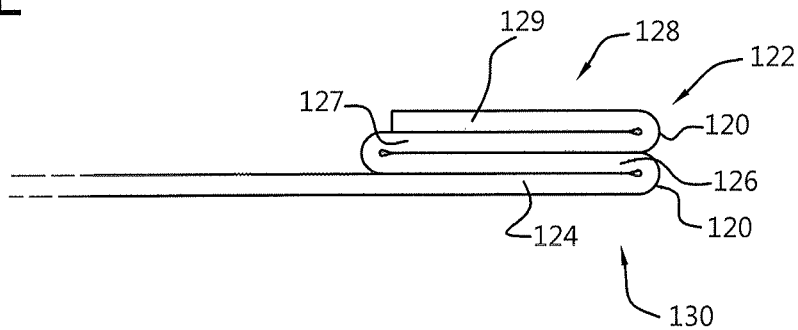
Figure 4F:
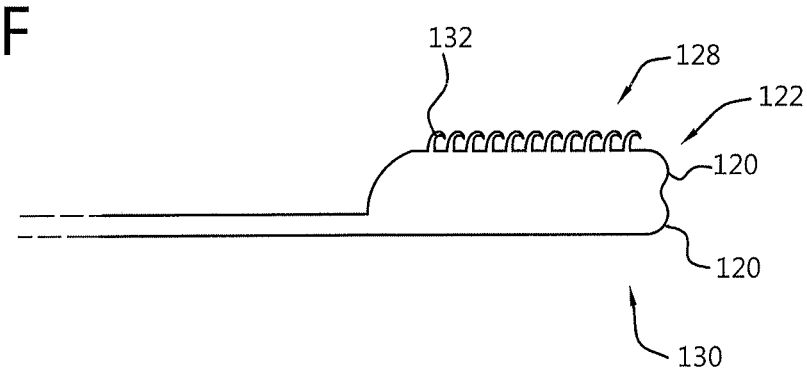

FIGS. 4A, 4C and 4E show three different embodiments of folding a side panel to obtain a multilayered lateral side portion 122. FIGS. 4B, 4D and 4F show the multilayered portions of FIGS. 4, 4C and 4E once subjected to a softening and forming operation.

The multilayered lateral side portion 122 of FIG. 4A is obtained by folding a part of the side panel such that a lateral side edge 120 is obtained and the multilayered lateral side portion 122 comprises a first layer 124 and a second layer 126 and comprises a first surface 128 and a second surface 130. In the embodiment shown in FIG. 4B, the multilayered portion 122 of FIG. 4A is subjected to a softening and forming operation. By the softening and forming operation the first layer 124 and the second layer 126 are connected to each other and preferably form one layer of material. At least part of the first surface 128 of the multilayered portion 122 is provided with surface protrusions 132 by the same softening and forming operation. The dimensions and relative dimensions of the surface protrusions 132 are exaggerated and not drawn to scale for illustrative purposes. The height of the surface protrusions 132 typically range between 0.1 and 0.5 mm and is for example equal to 0.3 or 0.4 mm.

As an alternative at least a part of the second surface 126 of the multilayered portion 122 may be provided with surface protrusions 132.

The multilayered lateral side portion 122 of FIG. 4C comprises a first layer 124, a second layer 126, and a third layer 127 and comprises a first surface 128 and a second surface 130. In the embodiment shown in FIG. 4D, the multilayered portion 122 of FIG. 4C is subjected to a softening and forming operation. By the softening and forming operation the first layer 124, the second layer 126 and the third layer 127 are connected to each other and preferably form one layer of material. At least part of the first surface 128 of the multilayered portion 122 is provided with surface protrusions 132 by the same softening and forming operation. As an alternative at least a part of the second layer 126 of the multilayered portion 122 may be provided with surface protrusions 132.

The multilayered lateral side portion 122 of FIG. 4E comprises a first layer 124, a second layer 126, a third layer 127 and a fourth layer 129 and comprises a first surface 128 and a second surface 130. In the embodiment shown in FIG. 4F, the multilayered portion 122 of FIG. 4E is subjected to a softening and forming operation. By the softening and forming operation the first layer 124, the second layer 126, the third layer 127 and the fourth layer 129 are connected to each other and preferably form one layer of material. At least part of the first surface 128 of the multilayered portion 122 is provided with surface protrusions 132 by the same softening and forming operation.

The surface protrusions 132 of FIGS. 4B, 4D and 4F can be arranged in a certain pattern.

Figure 5A:
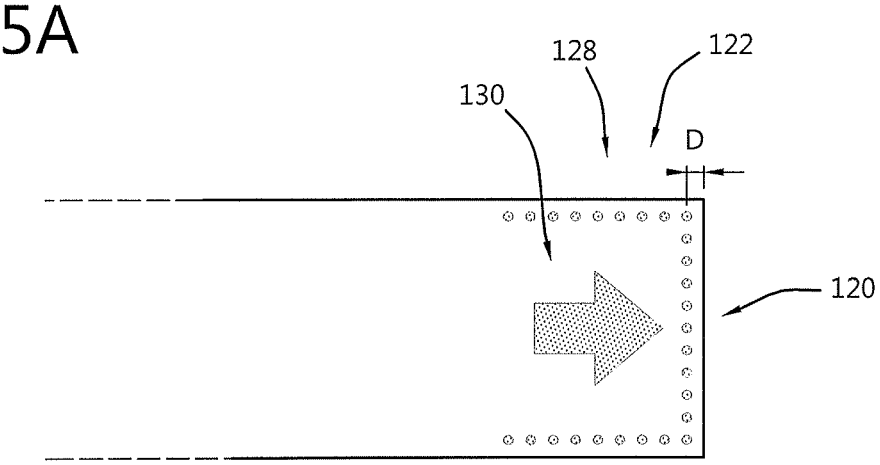
FIGS. 5A and 5B show two embodiments of visual indications at the second surface of a multilayered lateral side portion.
Figure 5B:
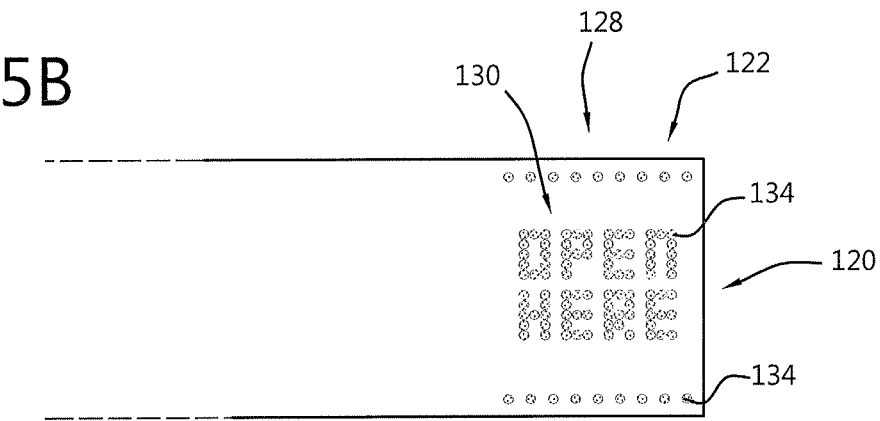

By providing surface protrusions 132 at the first surface 128 of the multilayered lateral side portion 122, the second surface 130 of the multilayered lateral side portion can be provided with one or more visual indications 134 (not shown in FIG. 4A, 4B, 4C). Some examples of visual indications 134 are given in FIG. 5A and FIG. 5B. In FIG. 5A the surface protrusions 132 shown in FIGS. 4A, 4B and 4C are arranged in a pattern, for example in a pattern forming an arrow, such that an arrow is created on the second surface 130. In FIG. 5B the surface protrusions 132 shown in FIGS. 4A, 4B and 4C are arranged in a pattern forming a text on the second surface 130.

When the surface protrusions 132, here shown as visual indications 134 are located at a distance D from the lateral side edge 120 of a side panel the multilayered side portion can function as a finger lift facilitating the opening of the side panels, for example of the belt portions of an absorbent article.

FIGS. 6A, 6C and 6E show three different embodiments of a Z-folding part of a side panel to obtain a multilayered portion 122. FIGS. 6B, 6D and 6F show the multilayered portion 122 once subjected to the softening and forming operation to connect the different layers of a multilayered portion 122 and to provide at least part of the first surface 128 of the multilayered portion 122 with surface protrusions 132. The dimensions and relative dimensions of the surface protrusions 132 are exaggerated and not drawn to scale for illustrative purposes. The height of the surface protrusions 132 typically range between 0.1 and 0.5 mm and is for example equal to 0.3 or 0.4 mm.

In the embodiments shown in FIGS. 6B, 6D and 6F the different layers of the multilayered portions 122 are preferably connected in such a way to form one layer of material. Preferably the second surface 130 of the multilayered portion 122 is provided with one or more visual indications by the same softening and forming operation.

The embodiments shown in FIGS. 6B, 6D and 6F are in particular suitable to be used as fastening tab as for example shown in FIG. 3.

It may be of particular interest to provide one or both side panels, for example one or both belt portions, of a belt diaper with one or more visual indication.

Figure 7:
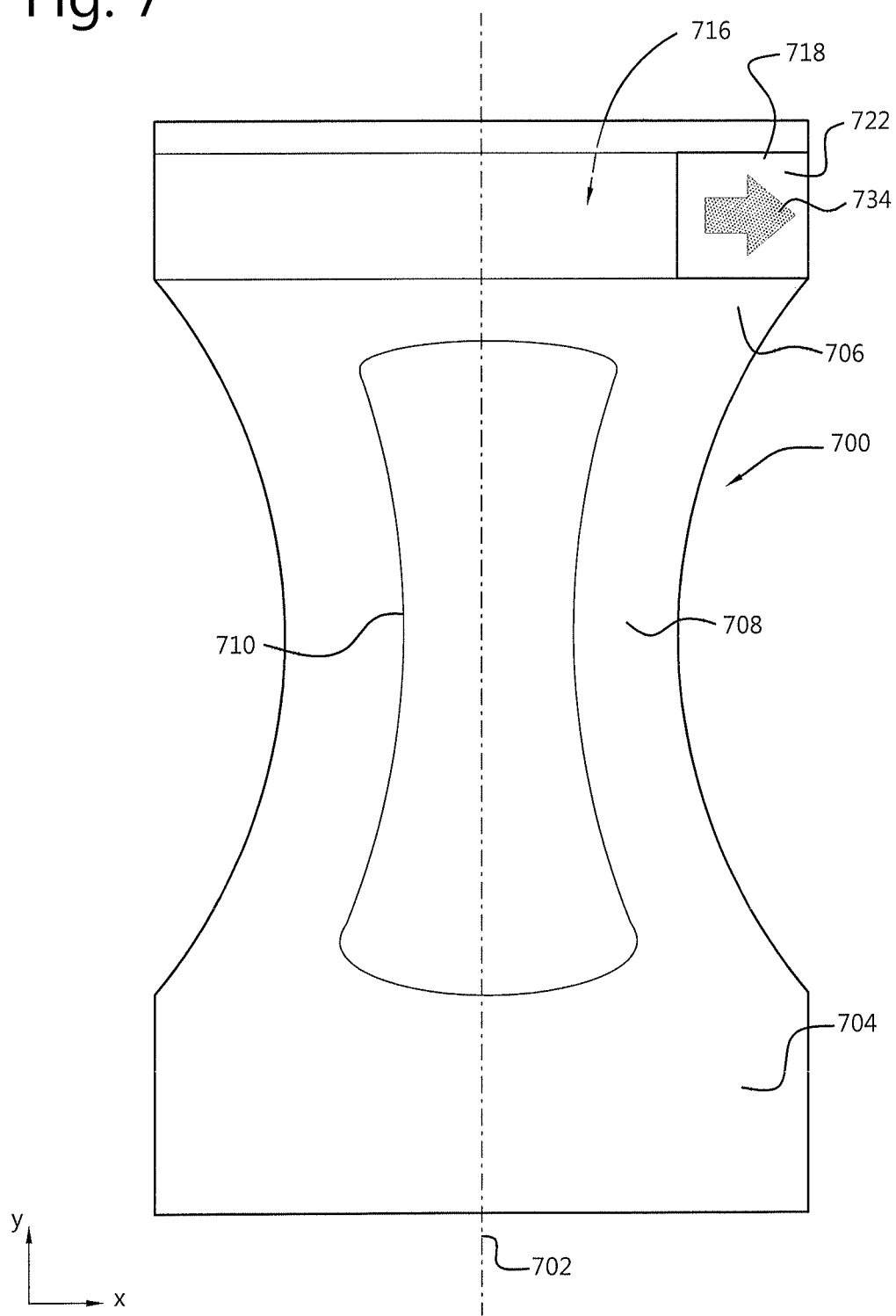
FIG. 7 shows a belt diaper according to an embodiment of the present invention before opening.

FIG. 7 shows a belt diaper 700, similar to the belt diaper shown in FIG. 2, from the side that is intended to face the user before opening of the belt diaper 700.

The belt diaper 700 comprises a first body portion 704, a second body portion 706, and a crotch portion 708 between the first body portion 704 and the second body portion 706. In use, the first body portion 704 (also referred to as the front portion) is located on the user's abdomen, whereas the second body portion 706 (also referred to as the rear portion) is located at the user's back.

The belt diaper 700 has a longitudinal direction, marked in FIG. 7 with Y and a lateral direction, marked in FIG. 7 with X. The belt diaper 700 has a longitudinal center line 702 extending along the longitudinal direction Y.

Preferably, an absorbent core 710 is disposed in the crotch portion 708. The second body portion 706 comprises two side panels 716, 718, more particularly two laterally extending belt portions 716, 718. As shown in FIG. 7, the first belt portion 716 and the second belt portion 718 are folded over the second body portion 706. The first belt portion 716 is thereby arranged on top of the second belt portion 718. The belt portions 716, 718 are intended to be wrapped around the waist of the user of the belt article 700. At least one of the belt portions 716, 718 is provided with a multilayered portion 722, here the first belt portion 718 is provided with the multilayered portion 722. One surface of the multilayered portion 722, i.e. the surface facing towards the second body portion 706 is provided with surface protrusions (not visible in FIG. 7), whereas the other surface of the multilayered portion 722, i.e. the surface facing towards the user (and facing away from the second body portion 706), is provided with a visual indication 734, for example with an arrow indicating how to open the belt portions 716, 718. The visual indication 734 may give instructions to the user on how to use the belt diaper, in particular how to open the laterally extending belt portions 716, 719. Furthermore the visual indication 734 may be very helpful for persons having a weaker eyesight.

Figure 8:
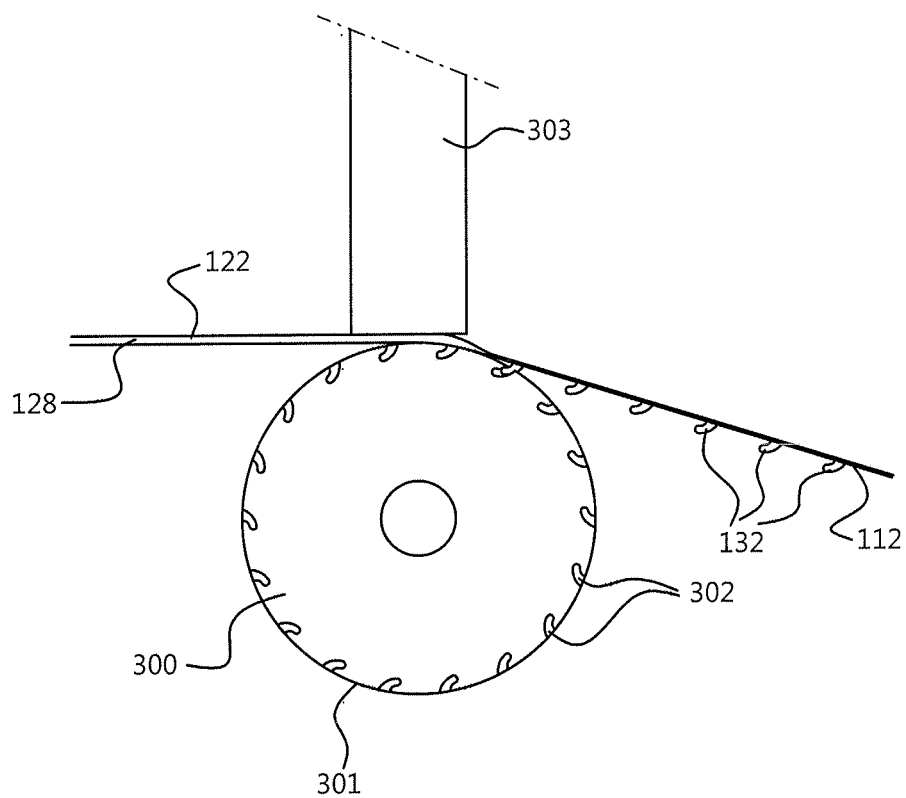
FIG. 8 shows an embodiment how to provide the multilayered portion shown in FIGS. 1 to 7 with surface protrusions.

FIG. 8 shows one example to provide a multilayered portion 122 as shown in FIGS. 1 to 7 with surface protrusions 132. FIG. 8 discloses a forming die 300, in form of a rotating moulding roll, which comprises a surface 301 provided with a plurality of cavities 302, at least some of said cavities 302 comprising a shape to produce surface protrusions 132. A first surface 128 of the multilayered portion 122 of one of the side panels of FIGS. 1 to 7 is in contact with said surface 301 of said forming die 300. During operation a vibration source 303 is positioned in close proximity to the surface 301 of the rotating forming die 300. The vibration source 303 may be a vibrating ultrasonic horn. The vibration source 303 apply energy to the at least one multilayered portion 122 to soften and form at least part of said at least one multilayered portion 122 in such a way that the first layer connects with the second layer, in case the multilayered portion 122 comprises two layers or with the additional layers if the multilayered portion 122 comprises more than two layers. The material of the multilayered portion 122 is forced into said cavities 302 to provide said first surface 128 of the multilayered portion 122 with surface protrusions 132.

While the present invention may be embodied in many different forms, a number of illustrative embodiments are described herein with the understanding that the present disclosure is to be considered as providing examples of the principles of the invention and such examples are not intended to limit the invention to preferred embodiments described herein and/or illustrated herein.

The invention claimed is:

1. An absorbent article having a longitudinal direction, a longitudinal center line extending along said longitudinal direction, and a lateral direction, said absorbent article comprising a first body portion, a second body portion and a crotch portion located between said first body portion and said second body portion, at least one of said first body portion or said second body portion comprises at least one side panel,
   said at least one side panel comprising at least one multilayered portion,
   said at least one multilayered portion comprising at least a first layer and a second layer,
   said at least one multilayered portion comprising a first surface and a second surface,
   said at least one multilayered portion being obtained by folding said side panel,
   said first layer and said second layer of said at least one multilayered portion being connected to each other and at least part of said first surface of said at least one multilayered portion being provided with surface protrusions,
   said surface protrusions being integrally made of material of said first layer and said second layer of said at least one multilayered portion such that said surface protrusions are integrally connected to at least one of said first layer and said second layer,
   wherein said at least one multilayered portion is subjected to a softening and forming operation to simultaneously connect said first layer and said second layer of said at least one multilayered portion and to provide said at least one multilayered portion with said surface protrusions.

2. The absorbent article according to claim 1, wherein said surface protrusions are adapted to be fastened to a landing zone of said absorbent article.

3. The absorbent article according to claim 1, wherein said at least one multilayered portion comprises a Z-folded portion.

4. The absorbent article according to claim 1, wherein said at least one multilayered portion comprises a multilayered lateral side portion obtained by folding at least a portion of said at least one side panel towards said longitudinal center line.

5. The absorbent article according to claim 2, wherein said second surface of said multilayered portion is provided with a visual indication, said visual indication being obtained by said softening and forming operation.

6. The absorbent article according to claim 1, wherein said surface protrusions comprise pins, straight pins, angled pins, curved pins, tapered pins, limbed or multi-limbed pins, hooks, limbed or multi-limbed hooks, mushroom shaped protrusions or palm tree shaped protrusions.

7. The absorbent article according to claim 1, wherein said at least one multilayered portion comprises at least a first layer, a second layer, and a third layer.

8. The absorbent article according to claim 1, wherein said absorbent article comprises a pant diaper, a belt diaper, or an all-in-one diaper.

9. An absorbent article having a longitudinal direction, a longitudinal center line extending along said longitudinal direction, and a lateral direction, said absorbent article comprising a first body portion, a second body portion and a crotch portion located between said first body portion and said second body portion, at least one of said first body portion or said second body portion comprises at least one side panel,
   said at least one side panel comprising at least one multilayered portion;
   said at least one multilayered portion comprising at least a first layer and a second layer,
   said at least one multilayered portion comprising a first surface and a second surface,
   said at least one multilayered portion being obtained by folding said side panel,
   said first layer and said second layer of said at least one multilayered portion being connected to each other and at least part of said first surface of said at least one multilayered portion being provided with surface protrusions,
   said surface protrusions being integrally made of material of said first layer and said second layer of said at least one multilayered portion such that said surface protrusions are integrally connected to at least one said first layer and said second layer.

10. The absorbent article according to claim 9, wherein said at least one multilayered portion is subjected to a softening and forming operation to connect said first layer and said second layer of said at least one multilayered portion.

11. The absorbent article according to claim 9, wherein said at least one multilayered portion is subjected to a softening and forming operation to provide said at least one multilayered portion with said surface protrusions.

12. The absorbent article according to claim 1, wherein said side panel comprises a proximal end having a first thickness of the material of the first layer and a distal end having a second thickness of the material of the first layer and the second layer, said proximal end is positioned nearer to the longitudinal center line than the distal end, wherein said second thickness is greater than said first thickness.

13. The absorbent article according to claim 12, wherein said first thickness of said proximal end is substantially uniform and said second thickness of said distal end is substantially uniform.

14. The absorbent article according to claim 13, wherein said second thickness is at least two times greater than the first thickness.

15. The absorbent article according to claim 12, wherein said at least one multilayered portion is positioned at said distal end.

16. The absorbent article according to claim 12, wherein the material of the first layer is the same material of the second layer.

17. The absorbent article according to claim 16, wherein in the distal end, the material of the first layer and the second layer are connected together so as to form one layer of material.

18. The absorbent article according to claim 9, wherein said side panel comprises a proximal end having a first thickness of the material of the first layer and a distal end having a second thickness of the material of the first layer and the second layer, said proximal end is positioned nearer to the longitudinal center line than the distal end, wherein said second thickness is greater than said first thickness.

19. The absorbent article according to claim 18, wherein said first thickness of said proximal end is substantially uniform and said second thickness of said distal end is substantially uniform.

20. The absorbent article according to claim 19, wherein said second thickness is at least two times greater than the first thickness.

21. The absorbent article according to claim 18, wherein said at least one multilayered portion is positioned at said distal end.

22. The absorbent article according to claim 18, wherein the material of the first layer is the same material of the second layer.

23. The absorbent article according to claim 22, wherein in the distal end, the material of the first layer and the second layer are connected together so as to form one layer of material.

* * * * *